US005118504A

United States Patent [19]

Clement et al.

[11] Patent Number: 5,118,504

[45] Date of Patent: Jun. 2, 1992

[54] HYPOALLERGENIC MOSS OILS AND METHODS FOR PREPARING SAME

[75] Inventors: Gérard Clement; Charles Ehret, both of Peymeinade; Martin Petrzilka, Grasse, all of France

[73] Assignee: Givaudan Roure (International) SA, Vernier/Geneva, Switzerland

[21] Appl. No.: 717,622

[22] Filed: Jun. 19, 1991

[30] Foreign Application Priority Data

Jun. 22, 1990 [EP] European Pat. Off. ....... 90.810468.0

[51] Int. Cl.[5] .......................... A61K 35/78; C11B 9/00

[52] U.S. Cl. ...................................... 424/195.1; 512/5; 426/542

[58] Field of Search .......................... 424/195.1; 512/5; 426/542

[56] References Cited

U.S. PATENT DOCUMENTS 4,308,401 12/1981 Willis .................................. 568/347

4,663,080 5/1987 Terajima .......................... 252/522 R 4,720,354 1/1988 Asakawa .......................... 252/522 R

FOREIGN PATENT DOCUMENTS 0202647 11/1986 European Pat. Off. .

OTHER PUBLICATIONS

Steinmetz E. F., Codex Vegetabilis 1957 Amsterdam #467.

Chem Pharm Bull 28 1917 (1980) Ohta.

*Primary Examiner*—Ronald W. Griffin

*Assistant Examiner*—Ralph Gitomer

*Attorney, Agent, or Firm*—Richard R. Muccino

[57] ABSTRACT

This invention pertains to hypoallergenic moss oils and a process for producing same which comprises reacting moss oil with an amino acid under mono-phasic conditions in solution and separating insolubilized allergenic substances.

7 Claims, No Drawings

HYPOALLERGENIC MOSS OILS AND METHODS FOR PREPARING SAME

BACKGROUND OF THE INVENTION

1. Field of the Invention

The present invention relates to hypoallergenic moss oils, more exactly it concerns a process to prepare such hypoallergenic moss oils.

2. Description of the Prior Art

European patent application no. 202,647, published Nov. 11, 1986, describes the preparation of hypoallergenic moss oils. Allergenic substances are removed from the moss oil by chromatography, solvent extraction, countercurrent partition, and/or membrane separation or catalytic hydrogenation and/or alkaline treatment. The allergenic substances removed were aldehydic compounds which include ethyl hematommate 1, ethyl chlorohematommate 2, atranorin 3, and chloratranorin 4.

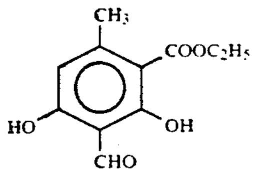

1

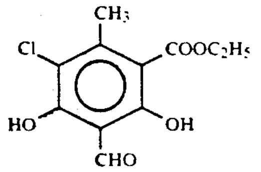

2

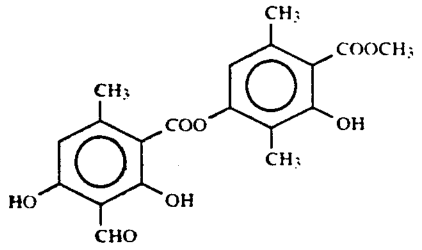

3

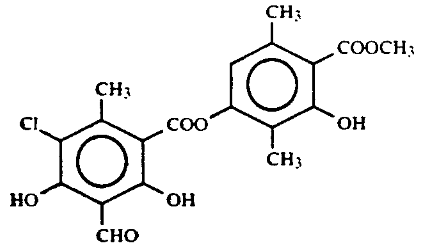

4

*S. Ohta et al., Chem Pharm. Bull.* 28 (1980), 1917 discloses that aldehydes in aqueous and organic solutions can be treated with aqueous sodium salt solutions of certain amino acids in order to separate the aldehydes as the Schiff base reaction products. This separation technique is not feasible for moss oils because emulsions result under such circumstances which can only be separated with great difficulty.

SUMMARY OF THE INVENTION

This invention pertains to hypoallergenic moss oils and a process for producing same which comprises reacting moss oil with an amino acid under mono-phasic conditions in solution and separating insolubilized allergenic substances.

DETAILED DESCRIPTION OF THE INVENTION

The process of the present invention comprises reacting moss oil with at least one amino acid under monophasic conditions in solution, preferably in substantially alcoholic solution and separating the insolubilized allergenic substances, including ethyl hematommate 1 ethyl chlorohematommate 2, atranorin 3, chloratrononin 4, atranol 5 and chloratranol 6. The moss oil is a starting moss oil, i.e., untreated moss oil, a concrete or an absolute thereof. The moss oils are obtained by solvent extraction of lichens including in particular the Oakmoss oil (*Evernia prunastri L.*) and the Treemoss oil (*Evernia furfuracea L.*).

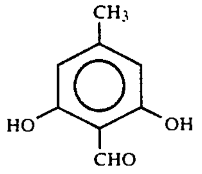

5

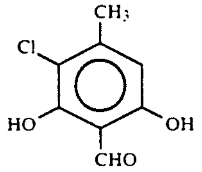

6

The novel procedure of the present invention overcomes difficulties with emulsions because the starting material is only soluble in organic solvents and the amino acid is only soluble in aqueous solutions. Furthermore, it was, surprisingly, found that the novel process seems not to organoleptically deteriorate the moss oil, in other words, none of the organoleptically active compounds whatsoever seem to be removed from the moss oil.

In the context of the present invention the concentrations of the aldehydes 1-6; are considered to be allergenic above about the levels shown in TABLE 1, and these concentrations are considered to be hypoallergenic below about the levels shown in TABLE 1.

TABLE 1

| Aldehyde | Allergenic moss oil % | Hypoallergenic moss oil % |
|---|---|---|
| Ethyl hematommate 1 | >1 | <1 |
| Ethyl chlorhematommate 2 | >0.05 | <0.05 |
| Atranorins 3 + 4 | >0.15 | <0.15 |
| Atranol 5 | >0.2 | <0.2 |
| Chloratranol 6 | >0.2 | <0.2 |

The convenient process parameters are as follows:

Amino acid: The preferred amino acids are represented by the general formula

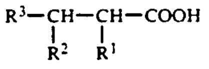

I wherein $R^1$=H or $NH_2$ $R^2$ = H or $CH_3$ $R^3$ = H, or $C_1$-$C_3$ alkyl, or $C_1$-$C_3$ alkylamino, or phenyl, and at least one amino radical is present in the $R^1$ or $R^3$ group.

The preferred amino acids are the naturally occurring (and the nature identical respectively) amino acids. Furthermore, preferred amino acids are those amino acids wherein the isoelectric point $P_I$ is between about 5.5 and about 10. In a preferred embodiment, the amino acid is selected from the group consisting of leucine, lysine, and phenylalanine. In another preferred embodiment, the amino acid is selected from the group consisting of alanine, glycine, isoleucine, etc. The preferred amino acids are those occurring naturally.

The mono-phasic conditions are achieved by working preferably in a substantially (preferably greater than about 95%) alcoholic solvent, e.g., alkanolic solvent, such as in methanol, ethanol, isopropanol, etc.

Concentration of amino acid in water: rather concentrated, e.g., about 30% to about 80% (w/w).

Amount of amino acid used: about 0.02 g to about 0.3 g, preferably about 0.04 g to about 0.1 g per gram of moss oil.

When the amino acid is used as the monohydrohalide, e.g., the hydrochloride, one molar equivalent of a base such as sodium hydroxide or potassium hydroxide is added.

pH: in the range indicated for $P_I$.

Temperature: from about 20° C. to about 80° C., preferably from about 70° C. to about 80° C., whereby a, preferably, hot organic solution of the starting moss oil is added to a, preferably, hot solution of the amino acid.

Convenient concentrations of starting materials in the alcoholic solutions:

concrete: about 5% to 40%, preferably about 10% to 15% (weight/weight) in alcohol.

absolute: about 5% to 40%, preferably about 10% to 15% (weight/weight) in alcohol.

Work up: simple filtration of the excess amino acid(s) and the Schiff bases.

In another embodiment, the present invention pertains to a hypoallergenic moss oil prepared by a process which comprises the steps of reacting moss oil with an amino acid under mono-phasic conditions in solution and separating insolubilized allergenic substances.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLES

Measurement of the Allergenicity

The presence or absence of allergy was in each case determined by conventional, fully established means, i.e., the MT (Maximization Test) using guinea pigs, the OET (Open Epicutaneous Test) using guinea pigs, and the RIPT (Repeated Insult Patch Test) using human subjects. The experimental data obtained served to construct TABLE 1.

The concentrations of products 1, 2, 5, and 6 are suitably measured by GC analysis, e.g., with an internal standard under the following conditions: Stationary phase: (silicone based) CPSIL 5 CB; vector gas: helium, 2 ml/minute; program: 100/270° C./minute.

The concentrations of the aldehydes 3 and 4 are suitably measured by HPLC, e.g., with an external standard, under the following conditions:

Stationary phase: RP18 (reverse phase) particle size 7 μm; column: 250×4.6 mm; mobile phase A: $H_2O$, pH = 2.8 ($H_3PO_4$); mobile phase B: açetonitrile; gradient 30 minutes, 80% A to 5% A; 10 minutes, 5% A; detection: UV at 260 nm.

EXAMPLE 1

Production of a Hypoallergenic Oakmoss Absolute from a Commercially Available Oakmoss Absolute Ethanol 96° (1.24 l) in a three necked, round-bottomed flask is stirred and a solution of lysine hydrochloride (6.25 g) and a one molar equivalent of sodium hydroxide (1.4 g) in 10 ml of distilled water, is added at room temperature, followed by the addition of leucine (6.25 g) in ethanol 96° (625 ml). After an additional stirring period of 30 minutes at room temperature, a solution of melted Oakmoss absolute (250 g, mp about 70° C.) in ethanol 96° (625 ml) is added and the total mixture is heated to reflux during one hour. After cooling to room temperature and further stirring for 30 minutes, the reaction mixture is filtered, at room temperature, through a Buchner funnel (on filter paper). The ethanol is removed by distillation under reduced pressure on a water bath without exceeding a temperature of 65° C. The analytical test results of the so obtained hypoallergenic Oakmoss absolute (240 g, yield>95%) are shown in TABLE 2.

TABLE 2

| Analysis | Starting Oakmoss absolute | Resulting Oakmoss absolute |
|---|---|---|
| Ethyl hematommate 1 | 3.53 | 0.90 |
| Ethyl chlorhematommate 2 | 1.44 | <0.05 |
| Atranorins (3 + 4) | 0.30 | 0.14 |
| Atranol 5 | 2.83 | <0.01 |
| Chloratranol 6 | 1.40 | <0.01 |

EXAMPLE 2

Production of a Hypoallergenic Oakmoss Absolute from Oakmoss Concrete

Ethanol 96° (900 ml) and melted Oakmoss concrete (150 g, mp about 70o C.) are placed in a three-necked, round bottomed flask. The mixture is cooled to 30° C. and, under stirring, a solution of lysine hydrochloride (3.75 g) neutralized with one molar equivalent of potassium hydrochloride (85%) (1.35 g) in 6 ml of distilled water, and leucine (3.75 g) are added at room temperature. After an additional stirring period of 30 minutes the total mixture is heated to reflux during one hour. After cooling to room temperature and further stirring during 30 minutes, the reaction mixture is cooled to −15° C. and filtered through filter paper. The ethanol is removed by distillation under reduced pressure on a water bath without exceeding a temperature of 65° C. The analytical results of the so obtained hypoallergenic Oakmoss absolute (110 g, yield=73% concrete) are shown in TABLE 3.

TABLE 3

| Analysis | Starting Oakmoss concrete | Resulting Oakmoss absolute |
|---|---|---|
| Ethyl hematommate 1 | 2.40 | 1.02 |
| Ethyl chlorhematommate 2 | 0.36 | <0.01 |
| Atranorins (3 + 4) | 4.00 | 0.12 |
| Atranol 5 | 0.57 | <0.01 |
| Chloratranol 6 | 0.46 | <0.20 |

EXAMPLE 3

Production of a Hypoallergenic Treemoss Absolute from a Commercially Available Treemoss Absolute The procedure is as described in Example 1, except that "Oakmoss absolute" was replaced by "Treemoss absolute". The analytical results of the so obtained hypoallergenic Treemoss absolute (250 g, yield about 100% absolute) are shown in TABLE 4.

TABLE 4

| Analysis | Starting Treemoss absolute | Resulting Treemoss absolute |
|---|---|---|
| Ethyl hematommate 1 | 2.26 | 0.19 |
| Ethyl chlorhematommate 2 | 0.51 | <0.01 |
| Atranorins (3 + 4) | 0.17 | 0.15 |
| Atranol 5 | 0.70 | <0.01 |
| Chloratranol 6 | 0.62 | <0.13 |

The invention being thus described, it will be obvious that the same may be varied in many ways. Such variations are not to be regarded as a departure from the spirit and scope of the invention and all such modifications are intended to be included within the scope of the following claims.

We claim:

1. A process for producing hypoallergenic moss oils which comprises:

(a) reacting moss oil with an amino acid under monophasic conditions in solution, wherein the ratio by weight of moss oil to amino acid is from about 1:0.02 to about 1:0.3, the temperature of the reaction is in the range from about 20° C. to about 80° C., and the amino acid has the general formula:

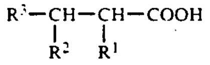

wherein $R^1$=H or $NH_2$ $R^2$=H or $CH_3$ $R^3$=H, or $C_1$-$C_3$ alkyl, or $C_1$-$C_3$ alkylamino, or phenyl, and at least one amino radical is present in the $R^1$ or $R^3$ group;

(b) separating insolubilized allergenic substances; and (c) recovering the hypoallergenic moss oil.

2. The process according to claim 1, wherein the solution is an alcoholic solution selected from the group consisting of methanol, ethanol, and isopropanol.

3. The process according to claim 2, wherein the solution is an ethanol solution.

4. The process according to claim 1, wherein the amino acid has an iso-electric point ($P_I$) in the range from about 5.5 to about 10.

5. The process according to claim 1, wherein the amino acid is selected from the group consisting of leucine, lysine, and phenylalanine.

6. The process according to claim 1, wherein the amino acid is selected from the group consisting of alanine, glycine, and isoleucine.

7. The process according to claim 1, wherein the temperature of the reaction is in the range from about 70° C. to about 80° C.

* * * * *